United States Patent [19]

Bays et al.

[11] Patent Number: 4,921,498

[45] Date of Patent: * May 1, 1990

[54] METAL CORE OSSICULAR REPLACEMENT PROSTHESIS

[75] Inventors: F. Barry Bays, Seminole, Fla.; Sam R. Marchand, Memphis, Tenn.

[73] Assignee: Richards Medical Company, Memphis, Tenn.

[*] Notice: The portion of the term of this patent subsequent to Apr. 18, 2006 has been disclaimed.

[21] Appl. No.: 396,059

[22] Filed: Aug. 21, 1989

Related U.S. Application Data

[63] Continuation of Ser. No. 486,268, Apr. 18, 1983, Pat. No. 4,871,364.

[51] Int. Cl.⁵ .............................. A61F 2/18
[52] U.S. Cl. ................................... 623/10
[58] Field of Search ................... 623/10, 11, 12, 16, 623/66

[56] References Cited

U.S. PATENT DOCUMENTS

| | | | |
|---|---|---|---|
| 3,473,170 | 7/1967 | Haase et al. | 623/10 |
| 3,710,399 | 1/1973 | Hurst | 623/10 |
| 3,909,852 | 10/1975 | Homsy | 623/10 |
| 3,986,212 | 10/1976 | Sauer | 623/16 |
| 3,987,789 | 10/1976 | Timm et al. | 623/66 |
| 4,281,419 | 8/1981 | Treace | 623/10 |

*Primary Examiner*—David J. Isabella
*Attorney, Agent, or Firm*—Pravel, Gambrell, Hewitt, Kimball & Krieger

[57] ABSTRACT

This invention is an ossicular replacement prosthesis made of porous polymeric material with a metal core of the type that includes a head portion for fitting against the tympanic membrane and a shaft for bridging the middle ear to provide conduction of sound to the middle ear.

4 Claims, 1 Drawing Sheet

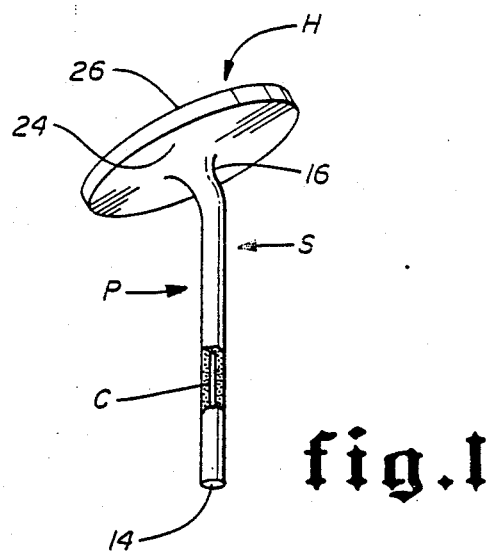
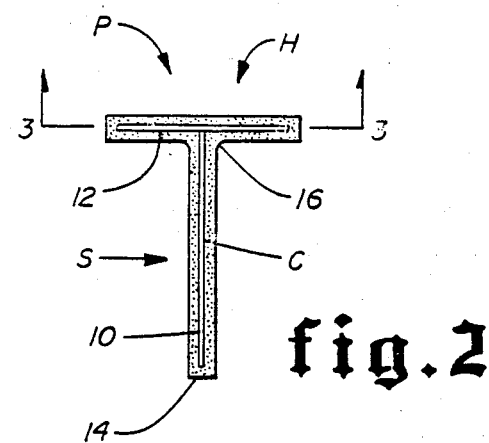
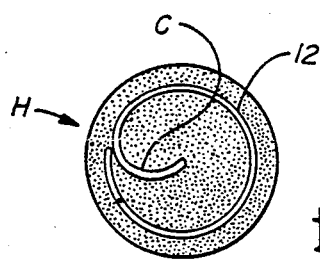
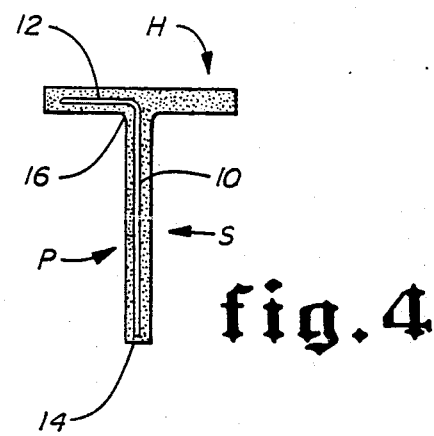
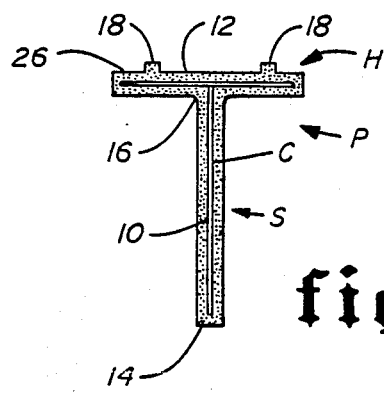
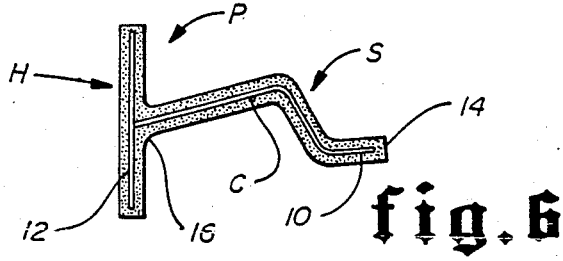
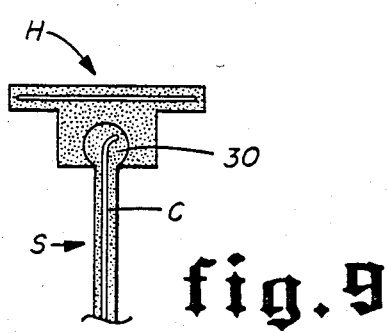
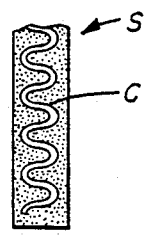

METAL CORE OSSICULAR REPLACEMENT PROSTHESIS

BACKGROUND OF THE INVENTION

This invention relates to prosthetic devices used to replace all or part of the ossicular structure of the middle ear.

In the human ear, sound entering the external auditory canal strikes the tympanic membrane, or ear drum, causing the membrane to vibrate. The vibrations of the tympanic membrane are transmitted through three ossicles in the middle ear, known as the malleus, incus and stapes, to an opening in the bony wall of the inner ear called the oval window. In the inner ear, the vibrations are transduced to nerve impulses that are deciphered in the brain. When the ossicular structure of the middle ear is removed or damaged, hearing is lost.

A variety of prostheses has been developed to replace the ossicular structure of the middle ear. Typically, the prosthesis is a one piece device with a head portion that is adapted to fit against the tympanic membrane and a shaft adapted to bridge the gap across the middle ear to contact at its distal end the oval window, or any remaining portion of the ossicular structure. Several such devices are shown in U.S. Pat. Nos. 3,473,170; 3,909,852 and 4,052,754.

The prostheses were found to perform best when they were constructed from a material that would permit tissue ingrowth from the tympanic membrane to anchor the head portion of the device. Likewise, when the prosthesis contacted the oval window, tissue in growth could anchor the distal end of the shaft. A porous polyethylene sold by Richards Medical Company under the name "PLASTI-PORE" as well as other porous polymeric materials became the preferred materials for use in such prosthesis because they possessed the requisite strength and density for performing the sound conducting function of the prosthesis, as well as the requisite porosity and biocompatibility to promote tissue ingrowth.

However, because the angle of the tympanic membrane with respect to the oval window varies from person to person, prosthesis constructed from the rigid, porous, high-density polymeric materials would not always fit well. A poor fit could affect the sound transmission efficiency of the device, or in some instances, lead to dislodgement or cause damage to the tympanic membrane or inner ear. Bending a prosthesis made of porous, high-density polymeric material caused uneven stress on the tissues of the ear, or even crumbling of the prosthesis. To overcome this problem, a prosthesis was developed by Richards Manufacturing Company, the corporate predecessor to the owner of the instant invention, that included a joint between the shaft and the head portion so that the head could be titled to conform to the angle of the tympanic membrane. This improved device is shown in U.S. Pat. No. 4,281,419. However, the movable joint required separate parts that could disarticulate and was relatively difficult to manufacture.

SUMMARY OF THE INVENTION

According to the present invention, a total ossicular replacement prosthesis (TORP) is constructed of porous polymeric material and includes a head portion adapted to fit against the tympanic membrane and a shaft adapted to bridge the middle ear. A metal core in the shaft increases the sound conductibility of the device and further makes the shaft and its connection with the head malleable or bendable so that the surgeon can bend the shaft of the prosthesis or the connection between the shaft and head to compensate for any irregular angles of the tympanic membrane. Because of the malleability feature, the prosthesis will keep its shape after it is fitted to the patient without crumbling or causing uneven stresses on the tissue.

Further, because the metal core is more dense than the porous polymeric material used to form the remainder of the prosthesis, the prosthesis constructed according to the present invention will conduct sound more efficiently than the prior art. The metal core can be arranged in the head portion of the prosthesis in, for example, the shape of a spiral, and connected to the core in the shaft to enhance the sound conduction throughout the entire prosthesis.

BRIEF DESCRIPTION OF THE DRAWINGS

For a better understanding of the present invention, reference may be made to the following description of several exemplary embodiments, taken in conjunction with the accompanying drawings, in which:

FIG. 1 is a perspective view of a prosthesis constructed according to the present invention showing a bent shaft with a portion of the shaft cut away to expose the metal core;

FIG. 2 is a longitudinal, sectional view of one embodiment showing a reinforcing wire in the shaft and head;

FIG. 3 is a top sectional view taken along the line 3—3 of FIG. 2;

FIG. 4 is a longitudinal, sectional view of another embodiment where the reinforcing wire extends only partially through the head;

FIG. 5 is a longitudinal, sectional view of another embodiment showing the addition of spurs to the head;

FIG. 6 is a longitudinal, sectional view of another embodiment of the present invention showing a bent shaft;

FIG. 7 is a longitudinal, sectional view of another embodiment showing a distal flange connected to the shaft;

FIG. 8 is a longitudinal, partial sectional view of another embodiment showing the metal core having a sign-wave shape; and FIG. 9 is a longitudinal, partial sectional view of another embodiment showing the core terminating a ball of a joint between the head and shaft.

DETAILED DESCRIPTION OF EXEMPLARY EMBODIMENTS

Several exemplary embodiments of the ossicular replacement prosthesis taught by the present invention will be described in detail with reference to the drawings. The prosthesis is referred to generally in the drawings by the letter P. The prosthesis P includes a head portion H, a shaft S and a metal core C.

As shown in FIG. 1, the head portion H of the prosthesis P is a disc-shaped member with an essentially flat top surface 26 and an essentially flat bottom surface 24. The shaft S extends from the bottom surface 24 of the head portion H such that the proximal end 16 of the shaft S abuts near the center of the head portion H. The metal core C extends inside the prosthesis P from the distal end 14 of the shaft S into the head portion H.

As shown more clearly in FIG. 2, the metal core C extends inside both the head portion H and the shaft S of the prosthesis P. The section of the metal core C that is within the head portion H of the prosthesis P is referred to as the head core 12; and the section that is inside the shaft S is referred to as the shaft core 10. The metal core C must run continuously from the head portion H through the shaft S in order to provide for enhanced conduction of sound to the inner ear and to impart malleability to the shaft S of the prosthesis P, especially at the connection between the shaft S and head H.

By including a head core 12 that extends throughout a substantially portion of the head H, such as in the shape of a spiral as shown in FIG. 3, the sound conduction properties of this prosthesis P are enhanced by the improved coupling of the dense metal core C to the tympanic membrane (not shown). Also, the spiral head core 12 serves as a suitable anchor for the shaft core 10 to assure that the shaft S can be bent as required by the angle of the tympanic membrane without causing crumbling near the proximal end 16 of the shaft S that could be caused by a poorly anchored metal core C.

However, as shown in FIG. 4, the head core 12 will suitably anchor the shaft core 10 in a variety of simpler configurations, such as a simple strand of metal. It will be appreciated that considerations of the user balancing the desired efficiency of sound conduction and the ease of manufacture, should determine the configuration of the head core 12.

The shaft core 10 extends from the head core 12 longitudinally through the proximal end 16 of the shaft S and through the shaft S. Generally, in order to enhance the sound conduction properties of the prosthesis P, the shaft core 10 extends the entire length of the shaft S from the proximal end 16 to the distal end 14. However, the prosthesis P will perform satisfactorily for many applications even when the shaft core 10 does not extend the full length of the shaft S so long as the metal core C is sufficiently anchored in the shaft S to allow bending near the proximal end 16 as shown in FIG. 1.

The sound conduction properties of the prosthesis P can be enhanced by constructing a convoluted shaft S as shown in FIG. 6. The natural ossicular structure of the inner ear amplifies the vibrations of the tympanic membrane because of the convoluted arrangement of the three ossicles. Because of the enhanced density and malleability of the prosthesis P according to the present invention, the shaft S can be convoluted to closely approximate the structure and accordingly the amplifying effect given by the natural ossicular structure.

Further, as shown in FIG. 7, the prosthesis P can be constructed with a distal flange 20 that is adapted to fit against the oval window. In some situations, the distal flange will provide superior sound coupling between the prosthesis P and the inner ear because of a greater area of contact. The distal flange 20 also provides for more extensive tissue ingrowth than the small distal end 14 of the shaft S. As is shown in the drawings, the metal core C extends into the distal flange 20 in a manner similar to that described above for the head portion H. The section of the metal core C that is inside the distal flange 20 is referred to as the flange core 22. The size of the distal flange 20 can be adapted to suit the needs of the patient or preference of the surgeon; thus, it need not be the same size as the head portion H as shown in FIG. 7.

As shown in FIG. 5, the fit and tissue ingrowth provided by the prosthesis P constructed according to the present invention can be further enhanced by one or more spurs 18 projecting from the top surface 26 of the head portion H. The spurs 18 improve the ability of the surgeon to position the prosthesis P on the tympanic membrane or, in the case of a similar spur (not shown) on the distal flange 20, on the oval window by preventing slippage during implantation. Further, the spurs 18 provide for a superior bond between the tissue and the prosthesis P after tissue ingrowth has occurred.

The prosthesis of the present invention can be manufactured by first forming the metal core C from metal, such as Type 316L stainless steel wire up to 0.008 inches in diameter, and then molding the porous polymeric material over the metal core C to form the head portion H and the shaft S of the prosthesis P. It has been found that the stainless steel wire used for the metal core C is compatible with the molding process. The prosthesis can be molded in two stages where the shaft and head are formed separately or in one stage where they are formed at the same time. Of course, other methods of manufacture may be used such as slowly driving or otherwise inserting the metal core into the pre-shaped prosthesis so that the metal core C fits closely inside the prosthesis P and so that the prosthesis P does not crumble during manufacture. The dimensions of the prosthesis P are determined by the size of the middle ear as is known in the art.

The metal core C can be formed in a wavy, sine-wave type shape as shown in FIG. 8 for providing a stronger mechanical bond between the wire and the porous polymeric material. The outer surfaces of the sine-wave pattern should not be greater than one-half the diameter of the shaft S to ensure that the wire does not extend to the outer surface of the shaft S. This configuration can be used in both the shaft S and head H of the prosthesis. The outer surface of the core could also be roughened for a stronger mechanical bond.

As shown in FIG. 9, the prosthesis of U.S. Pat. No. 4,281,419 can be modified in accordance with the invention to include a wire core C in both the shaft S and head H. The core C can terminate in the ball 30 of the joint between the head H and shaft S and still provide superior sound transmission properties.

Accordingly, a novel ossicular replacement prosthetic device is presented that eliminates the need for moving parts that can disarticulate while allowing the necessary adaptability to fit any angle of the tympanic membrane encountered by the surgeon. Further, the prosthesis taught by this invention retains the desirable characteristics of porous polymeric materials for implants while improving upon the sound conducting properties of the ossicular replacements known in the prior art.

The foregoing disclosure and description of the invention are illustrative and explanatory thereof, and various changes in the size, shape and materials, as well as in the details of the illustrated construction may be made without departing from the spirit of the invention.

We claim:

1. An ossicular replacement implant comprising:
   (a) a body including elongated shaft and enlarged head portions, said shaft and head portions being formed of a biocompatible porous material;
   (b) a core encased within said head and shaft portions of said body, the core being formed of a length of bendable metal and including an elongated core shaft located within said elongated shaft of said body portion and further including a first end forming a head extending substantially radially from the axis of the elongated shaft and engaging the head portion of the body, the core extending continuously from the shaft portion to the head portion of the body for connecting them together and allowing them to be oriented at a selected angle relative to each other by bending the bendable metal.

2. The implant of claim 1, in which said core is substantially symmetrical within the body.

3. The implant of claim 2, in which said body is formed of a biocompatible porous polymer.

4. The implant of claim 2, wherein the elongated shaft and head portions of said body are formed as an integral one-piece unit.

* * * * *